United States Patent [19]

Frohn

[11] Patent Number: 4,676,254

[45] Date of Patent: Jun. 30, 1987

[54] DEVICE FOR MONITORING PERIODS OF OVULATION

[76] Inventor: Hermann J. Frohn, Kirchplatz 5, D-5460 Linz am Rhein, Fed. Rep. of Germany

[21] Appl. No.: 837,008

[22] Filed: Mar. 6, 1986

[30] Foreign Application Priority Data

Mar. 16, 1985 [DE] Fed. Rep. of Germany ....... 3509503

[51] Int. Cl.$^4$ ............................................. A61B 10/00
[52] U.S. Cl. .................................... 128/736; 128/738; 128/778
[58] Field of Search ............... 128/736, 738, 903, 775, 128/778; 33/511–512

[56] References Cited

U.S. PATENT DOCUMENTS

| | | | |
|---|---|---|---|
| 3,583,389 | 6/1971 | Harvey | 128/736 |
| 3,893,111 | 7/1975 | Cotter | 128/736 X |
| 4,204,548 | 5/1980 | Kurz | 128/778 |
| 4,387,724 | 6/1983 | Zartman | 128/738 X |
| 4,411,274 | 10/1983 | Wright | 128/738 |
| 4,471,354 | 9/1984 | Smith | 128/736 X |
| 4,515,167 | 5/1985 | Hochman | 128/738 X |

FOREIGN PATENT DOCUMENTS

| | | | |
|---|---|---|---|
| 0090327 | 10/1983 | European Pat. Off. | 128/736 |
| 0117818 | 9/1984 | European Pat. Off. | 128/778 |
| 3231863 | 3/1984 | Fed. Rep. of Germany | 128/778 |

OTHER PUBLICATIONS

Klaften; "Utero-Thermometry"; *Journal of Clin. Endocrinology*, vol. 4, No. 4, 4-1944, pp. 159-165.

*Primary Examiner*—Lee S. Cohen
*Assistant Examiner*—Angela D. Sykes
*Attorney, Agent, or Firm*—Spensley Horn Jubas & Lubitz

[57] ABSTRACT

The present invention teaches a device for monitoring periods of ovulation, which comprises a housing containing a thermometer that is introducible into the uterus. Temperature values are inputted into a memory at predetermined time intervals. Thus, for long periods of time, body temperature may be measured accurately and in constant intervals. In response to an external command signal, a transmitter and a receiver causes the stored temperature values to be retrieved. In this way, a complete chart of body temperature may be obtained in order to accurately determine a woman's ovulatory period, thereby allowing her to intentionally avoid or permit conception.

13 Claims, 3 Drawing Figures

DEVICE FOR MONITORING PERIODS OF OVULATION

BACKGROUND OF THE INVENTION

The present invention relates to a device for measuring the body temperature, and more particularly to a device for monitoring the ovulatory periods of a woman.

For many women, the use of birth control pills is not a viable means for avoiding pregnancy. Although the pill is a widely popular means of birth control, these women are either allergic to the pill or are religiously opposed to the use of artificial controls. As a result, these women seek more natural ways of birth control.

It is well known that during a woman's period of ovulation, her body temperature changes, typically rising, during which time the woman may become pregnant. Thus, the more precise a woman can determine her ovulatory period, the better she can achieve or avoid conception.

Unfortunately, the widespread use of this natural method of birth control has been hampered by the often lengthy, difficult and time consuming procedures required to effectively chart a woman's body temperature for birth control purposes. For example, a woman's ovulatory period is best determined by measuring and recording daily her basal body temperature. Since the basal body temperature is the body's temperature at rest, this means that immediately after awakening and before any significant activity, a woman needs to insert a thermometer into her vagina, wait several minutes, and record her body temperature. As a result of this complex daily procedure, a woman is more apt to forego recording her more useful vaginal temperature and instead keep track of her oral temperature. In addition, the accurate reading of a thermometer is often difficult, particularly in these circumstances where a tenth of a degree is significant. More significantly, a busy working woman that is late in getting up is likely to forget or neglect taking her basal body temperature. For that reason, complete data of a woman's basal body temperature over a lengthy period of time is rarely obtained in practice. Furthermore, later measurements of her body temperature are inaccurate substitutes for her basal body temperature, thereby making a determination of her ovulatory periods less precise.

An object of the present invention is to provide a device which automatically measures and records body temperature at a high accuracy and in regular fixed intervals to obtain a reliable table of body temperature data over a long period of time.

Another object of the present invention is to provide a device which measures and records a woman's uterine temperature, thereby providing more significant data for precisely determining her ovulatory period.

SUMMARY OF THE INVENTION

In accordance with the present invention, these and other objectives are achieved by providing a temperature measuring and recording means containable in a housing that is itself introducible into a body. The temperature measuring and recording means features a data memory controlled by a timer so that temperature values are stored at predetermined time intervals. It further features a transmitter and a receiver, responsive to an external signal, for retrieving stored data from the data memory.

The preferred method of use of the present invention's device will now be explained. The inventive device may be introduced into a woman's body by inserting it into her uterus. Alternatively, the inventive device may also be implanted in the uterus in a similar fashion as contraceptive spirals. As the temperature measuring means is completely embedded in her uterus, it assumes her uterine temperature. At predetermined intervals, e.g., once a day, the current temperature value is recorded and stored in an electronic memory. Over a period of time, therefore, a number of temperature values are stored. An external command signal causes the memory to supply the stored temperature values to an external device, which prints them out or renders them readable by other means. In this way, a reliable time curve of uterine temperature may be obtained from which a woman's ovulatory period may be accurately determined. As a result, the device may be used to assist women in determining periods of time when they are likely or not likely to conceive.

The implantation of the device will now be explained. The device is implanted in the uterus by means of one or more elongated holding members extending from the housing and adapted to be anchored in an oviduct. The housing is introduced into the uterus through a hollow tube and is guided toward the oviducts to ensure that the holding members enter one of the oviducts for anchoring in the oviduct's walls. The use of the hollow tube enables the device to be easily and safely introduced into the body of a patient.

The housing may later be extracted by a thread fastened to it, which facilitates its removal from the uterus. During the removal of the housing from the body, however, careful attention must be paid so that the housing member or members do not traumatize the uterine wall. In addition, there is the further risk that a fertilized ovum present in the uterus may be injured by a holding member. To avoid this risk, a preferred embodiment provides that the holding members be retractable within the housing. The holding members are attached to a spring which biases the holding members toward a retracted position. The holding members, however, are kept in an anchoring position by a releasable locking means. The locking means may be released by an external command signal in order to retract the holding members into the housing prior to the removal of the housing from the uterus. To further minimize trauma, the housing is preferably shaped round, i.e., spherical or egg-shaped, and of sufficient size to accommodate the retracted holding members.

The present invention not only lends itself to monitoring ovulatory periods, but it may also be used generally for monitoring a sick patient's body temperature during periods of illness. Since this device may be implanted in the patient, it is particularly useful for bedridden patients at home who do not have or cannot afford anyone to watch over them. Since the retrieval of measured and stored data may be performed by wireless means, doctors may use an external device, which cooperates radiotelegraphically with the transmitter and receiver of the present invention, to periodically retrieve their patients' stored data and to advise their patients accordingly. Furthermore, the device may be adapted to measure and record body temperatures at shorter time intervals, e.g., hourly for short term illnesses.

BRIEF DESCRIPTION OF THE DRAWINGS

A detailed description of the invention will be made with reference to the accompanying drawings wherein.

DESCRIPTION OF THE PREFERRED EMBODIMENT

The following description is of the presently contemplated mode of carrying out the present invention. This description is not to be taken in a limiting sense; it is made merely for the purpose of illustrating the general principles of the invention since the scope of the invention is best defined by the appended claims.

Figure 1:
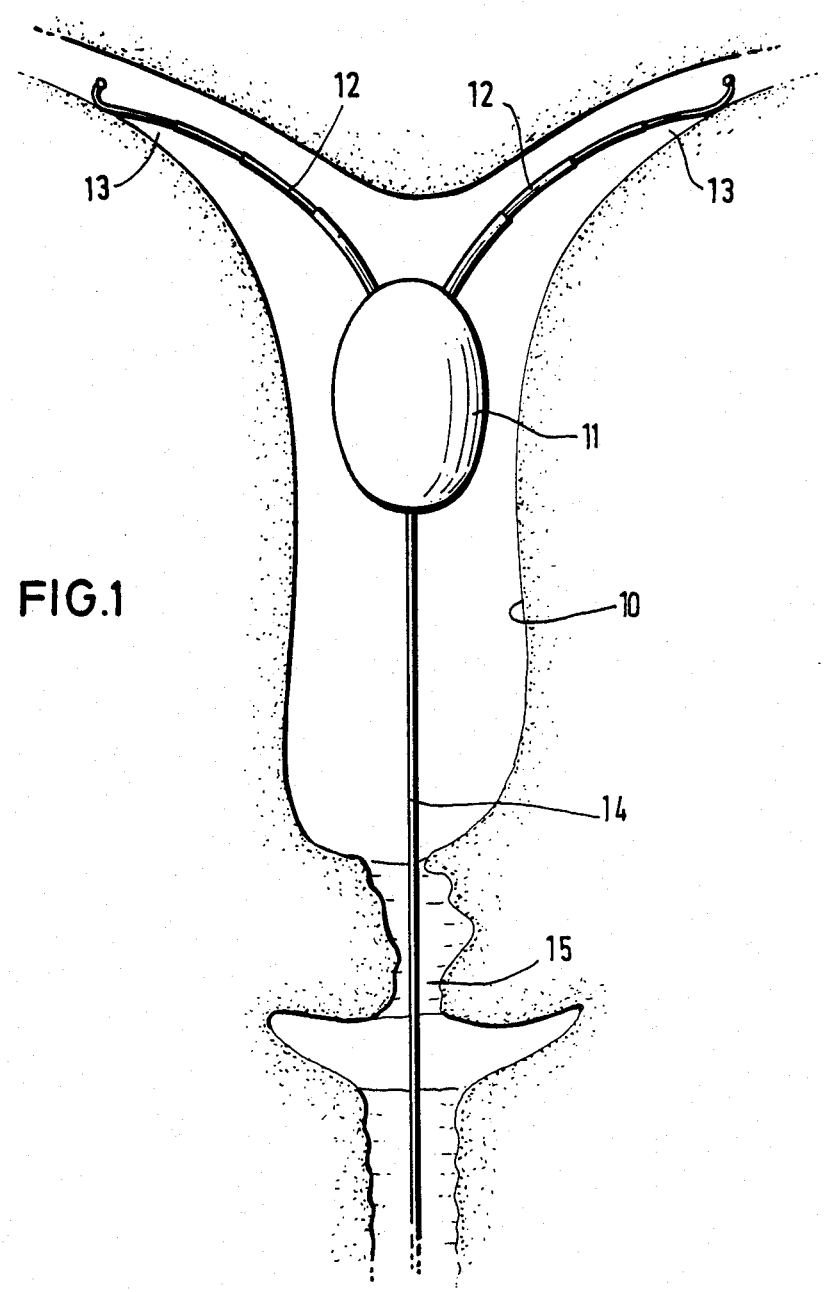
FIG. 1 shows the uterus with the inserted inventive device.

In the preferred embodiment the present invention is used to monitor uterine temperature. Referring to FIG. 1, the present invention comprises a housing 11 from which two elongated support members 12 project. These support members 12 extend into oviducts 13 and anchor housing 11 inside uterus 10. Opposite to holding members 12, thread 14 hangs down from housing 11 into the vaginal canal 15 to facilitate the later extraction of housing 11 out of the uterus. Housing 11 further comprises an electronic temperature measuring device 16, a memory means 17, a timer 18 and transmitting and receiving means 19. In addition, there is provided in housing 11 a battery 20 for supplying power to the aforementioned components.

Housing 11 is configured to be rotationally symmetric without any corners or edges, e.g., spherical or egg-shaped, so as to minimize any risk of trauma to the uterus. In addition, housing 11 should be as small as possible to more easily and safely insert the device into the uterus. Furthermore, housing 11 should be made of material tolerated by the human body.

The operation of the present invention, once it is implanted inside the uterus, will now be explained. Temperature measuring device 16 continuously produces a digital signal corresponding to the temperature of uterus 10. The digital signal is then stored in memory means 17 at predetermined time intervals in accordance with timer 18. Timer 18 supplies a digital timing control signal, i.e., every hour or once a day, which controls the rate that the temperature digital signal is being stored into memory means 17. Concurrently, the digital timing signal associated with the temperature signal is also being stored in memory means 17. In addition, the intervals at which the temperature values are received in memory means 17 may be changed by correspondingly changing the timing control signal of timer 18. Again, both the temperature values and the associated time values are digitally stored in memory means 17.

Figure 3:
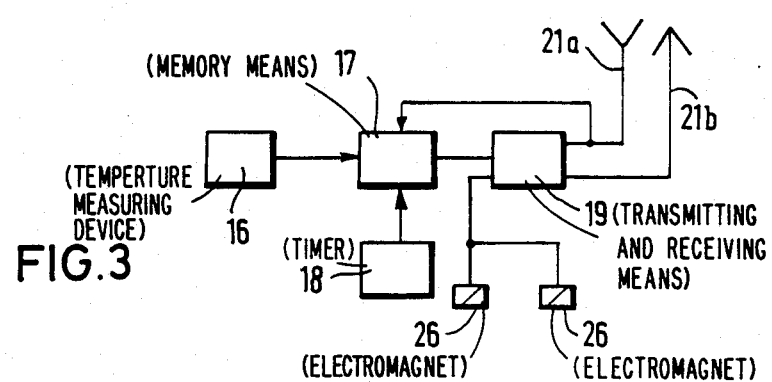
FIG. 3 shows a flow diagram of the device's operation.

Transmitting and receiving means 19 is preferably provided with receiving antenna 21a and transmitting antenna 21b as shown in FIG. 3, although one antenna may be used for both receiving and transmitting. A command signal supplied from an external device (not shown) is received by antenna 21a for retrieving the data from memory means 17. The stored temperature and time data are subsequently sent to transmitting and receiving means 19 so as to be emitted via the transmitting antenna 21b. The same external device may either store the data for later printing or print the data out immediately.

Figure 2:
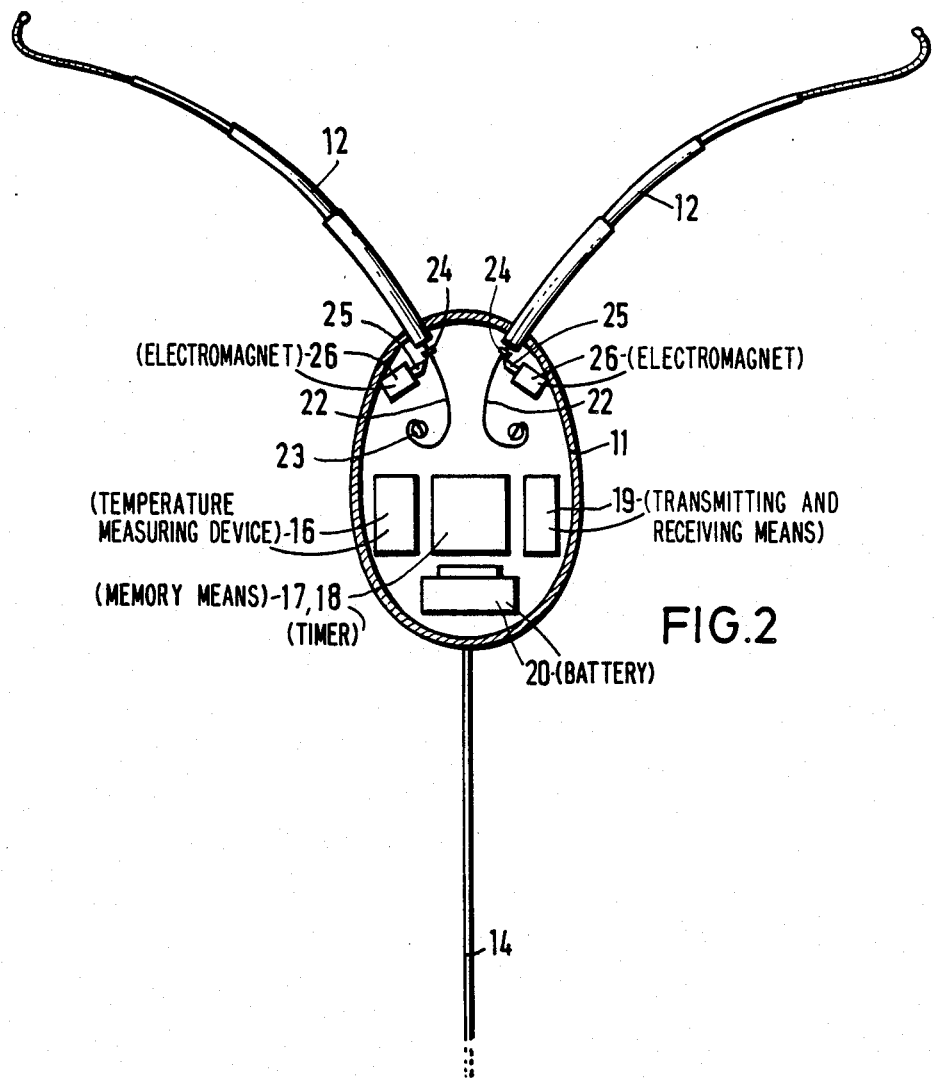
FIG. 2 shows a cross-sectional view of the device.

Retractable holding members 12, which anchor the present invention in uterus 10, are telescopic rods that extend out of housing 11 as illustrated in FIGS. 1 and 2. Holding members 12 are preferably made of a flexible material to minimize trauma to uterus 10. As seen in FIG. 2, springs 22 are of the coil type design and are attached at one end to each holding member 12. The other ends of springs 22 are secured to fixation points 23 of housing 11. Each of coil springs 22 tends to spirally wind itself about fixation point 23. Springs 22 are provided with projections 24, which are controllably engaged by retractable locking elements 25. When projections 24 are so engaged by locking elements 25, springs 22 are prevented from winding itself. Locking elements 25 additionally include springs (not shown) which extend locking elements 25 in unretracted positions in which attachments 24 are lockingly engaged.

An explanation of how the present invention's device may be removed will now be explained. Current pulses from electromagnets 26 cause locking elements 25 to retract, thereby disengaging attachments 24. The current pulses from electromagnets 26 are activated by a signal from transmitting and receiving means 19, which in turn may be initiated by a second external command signal. Disengaging attachments 24 in turn release springs 22, which wind about fixation points 23, causing each individual section of telescopic rods 12 to slide into one another and into housing 11. In this way, holding members 12 become completely retracted within housing 11. By further drawing thread 14, the device may then be easily removed from the body with minimal risk of injury to uterus 10.

What is claimed is:

1. A device for monitoring periods of ovulation by measuring uterine temperature, comprising:
    a housing, compatible with and configured to be easily insertable into a uterus through the vagina and the cervical canal;
    a temperature measuring means contained in said housing;
    a memory means contained in said housing for storing measured values of uterine temperature at predetermined time intervals;
    a transmitting and receiving means contained in said housing for transmitting, in response to a receipt of an external signal, said temperature values from said memory means; and
    an extractable holding member having means for anchoring said housing to an oviduct of said uterus.

2. A device according to claim 1 characterized in that said housing further comprises a pull thread for withdrawing said device from said uterus.

3. A device according to claim 1, further comprising biasing means, attached to said holding member, for retractably pulling said holding member into said housing, and
    a releasable locking means for maintaining said holding member in an extracted position.

4. A device according to claim 3 wherein said releaseable locking means is controllable by an external command signal.

5. A device according to claim 1, characterized in that said holding member is retractable with said housing for easily withdrawing said housing from said uterus.

6. A device, implantable into and compatible with a hollow organ body having an internal surface, for the long term monitoring of the temperature of said body, comprising:
- a generally rounded housing containing no edges, implantable within said body;
- a temperature measuring means contained in said housing;
- a memory means contained in said housing for storing measured values of temperature of said body at predetermined time intervals;
- a transmitting and receiving means contained in said housing for transmitting, in response to a receipt of an external signal, said temperature values from said memory means; and
- an extractable holding member having means for anchoring said housing to the internal surface of said body.

7. A mounting for a device to be situated in a uterus, comprising:
- a housing insertable into a uterus
- an extractable holding member having means for anchoring said device to an oviduct of said uterus; said holding member being retractable within said housing.
- a spring attached to said holding member for retractably pulling said holding member into said housing; and
- a releasable locking means capable of engaging said holding member for maintaining said holding member in an extracted position.

8. A device according to claim 7, characterized in that said holding member is a flexible telescopic rod.

9. A device according to claim 7 wherein said releasable locking means is controllable by an external command signal.

10. A device according to claim 7 further comprising a pull thread attached to said device for withdrawing said device from said uterus.

11. A device according to claim 7 wherein said extractable holding member has no attachments other than said housing that would impede the insertion of said holding member substantially into said oviduct.

12. A device as claimed in claim 7 wherein said means for anchoring said device further comprises a curve in said holding member at a point of contact with said oviduct.

13. A device as claimed in claim 7, further comprising:
- biasing means attached to said holding member for retractably pulling said holding member into said housing.

* * * * *